United States Patent [19]
Qin et al.

[11] Patent Number: 6,080,420
[45] Date of Patent: *Jun. 27, 2000

[54] FIBRES OF COSPUN ALGINATES

[75] Inventors: Yimin Qin, Northwich; Denis Keith Gilding, Winsford, both of United Kingdom

[73] Assignee: Advanced Medical Solutions Limited, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/809,686

[22] PCT Filed: Sep. 26, 1995

[86] PCT No.: PCT/GB95/02284

§ 371 Date: Jun. 30, 1997

§ 102(e) Date: Jun. 30, 1997

[87] PCT Pub. No.: WO96/10106

PCT Pub. Date: Apr. 4, 1996

[30] Foreign Application Priority Data

| Sep. 29, 1994 | [GB] | United Kingdom | 9419572 |
| Jan. 26, 1995 | [GB] | United Kingdom | 9501514 |
| Aug. 18, 1995 | [GB] | United Kingdom | 9516930 |

[51] Int. Cl.[7] ........................................ A61K 9/70
[52] U.S. Cl. .......................... 424/443; 424/449; 424/484; 424/486; 424/488
[58] Field of Search ..................... 424/443, 449, 424/484, 486, 488

[56] References Cited

U.S. PATENT DOCUMENTS

| 5,144,016 | 9/1992 | Skjak-Braek | 536/3 |
| 5,230,853 | 7/1993 | Colegrove | 264/186 |
| 5,622,666 | 4/1997 | Struszczyk | 264/191 |
| 5,660,857 | 8/1997 | Haynes | 424/450 |

FOREIGN PATENT DOCUMENTS

| 0527271 | 2/1993 | European Pat. Off. | C08L 5/04 |
| 61-1289886 | 12/1986 | Japan | C07K 17/04 |

Primary Examiner—Thurman K. Page
Assistant Examiner—R. Bawa
Attorney, Agent, or Firm—Clifford W. Browning; Woodard, Emhardt, Naughton, Moriarty & McNett Patent and Trademark Attorneys

[57] ABSTRACT

Fibres which are useful in wound dressings comprising an alginate co-spun with at least one water soluble organic polymeric species (other than an alginate). Examples of such fibers comprise alginate and CMC.

28 Claims, No Drawings

FIBRES OF COSPUN ALGINATES

The present invention relates to alginate containing fibres which are useful particularly, but not exclusively, in the manufacture of wound dressings.

Alginates are a family of polymers which may be obtained from seaweed and which contain varying proportions of mannuronic and guluronic residues depending on the source of the polymer.

It is established practice to produce alginate fibres by spinning a solution of a soluble form of an alginate polymer into a gelation (or coagulation) bath in which an insoluble form of the alginate precipitates. Typically the soluble form of the polymer is the sodium salt and the bath contains calcium ions to produce insoluble calcium alginate. Fibres produced in this way have high absorbency and are used in the manufacture of wound dressings, e.g. for wet wounds such as pressure sores, leg ulcers, surgical incisions and donor sites where the primary function of the alginate is to absorb exudate.

The present invention relates to modified alginate fibres which are useful in wound dressings.

According to a first aspect of the present invention there is provided fibres comprising an alginate co-spun with at least one water soluble organic polymeric species (other than an alginate).

According to a second aspect of the invention there is provided a method of producing fibres comprising co-spinning a dope which contains dissolved alginate and at least one dissolved organic polymeric species (other than an alginate) into an aqueous coagulation bath which causes precipitation of fibres each comprised of the alginate and said other polymeric species.

The non-alginate polymer is preferably (but not necessarily) one having negative charges along the polymer chain, i.e. a polyanion. Alternatively the polymer may be uncharged.

Preferably the fibres comprise 70–95% by weight alginate and 5–30% by weight of the non-alginate polymer.

The incorporation of the water soluble non-alginate polymeric species into the fibres with the alginate allows useful fibres of modified properties to be obtained, as compared to the properties obtained in the alginate is the sole component of the fibres. The modified properties may, for example, be increased absorbency of the fibres.

Generally the fibres will comprise a major proportion by weight of the alginate, e.g. 50–95% by weight, and a minor proportion of the non-alginate polymeric species. The alginate may be one having a G-content of 35–70% and correspondingly an M-content of 65–30% by weight. Typically the alginate will be such that a 1% solution will have a viscosity of 30–300 cP, preferably 40–100 cP.

If the non-alginate polymeric species contains negatively charged groups, these may be provided, for example, by $COO^-$ or $SO_4^{2-}$ groups along the polymer chain.

In one embodiment of the invention, alginates may be co-spun with non-alginate species containing $COO^-$ groups along the chain, examples of which include polysaccharides, polycarboxyamino acids it is also possible to use acrylic acid and/or metharcrylic acid, or salts thereof (e.g. the sodium salt). More specific examples include pectin, carboxymethyl cellulose, N—,O-carboxymethyl chitosan (NOCC), carrageenan, xanthan, gellan, polyaspartic acid and polyglutamic acid.

The alginate may be co-spun with a non-alginate polymer containing $COO^-$ groups which results in a fibre having increased absorbency as compared to one prepared from the alginate alone. Examples of such non-alginate polymers which result in increased absorbency include carboxymethyl cellulose, carrageenan, polyacrylic acid and NOCC. Thus fibres of improved absorbency may comprise 70–90% alginate and a total of 5–30% of at least one of CMC, carrageenan, polyacrylic acid and N,O,-carboxymethyl chitosan (NOCC) or O-carboxymethyl chitosan (OCC).

If the alginate is co-spun with pectin, fibres are produced which, when made into (and used) as a wound dressing, soften dry wounds, start autolysis procedures, and assist debridement macrophage stimulation. Preferably the pectin comprises 5–30% (more preferably 10–20%) by weight of the fibres.

The presence of pectin (which consists chiefly of partially methoxylated polygalacturonic acids) does reduce the absorbency of the fibres. Therefore a balance may need to be struck between the absorbency of the fibres (as provided by the alginate) and the wound healing properties thereof (as provided by the pectin). It is possible to co-spin alginate, pectin and at least one non-alginate polymer bearing negative charges which boosts absorbency. Thus fibres may be produced by co-spinning alginate, pectin and either CMC, NOCC or OCC, typically in a ratio of 60%–80% alginate, 10%–20% pectin and 10%–20% CMC, NOCC or OCC.

Further examples of fibres which may be produced in accordance with the first embodiment of the invention include a mixture of components producing a product which is a cross between an alginate and a hydrocolloid. Thus, for example, it is possible to spin such alginate/hydrocolloid products from solutions of alginate, gelatin, pectin, and CMC, e.g. in the following amounts:

| Alginate | Gelatin | Pectin | CMC |
| --- | --- | --- | --- |
| 45 | 10 | 25 | 20 |
| 35 | 10 | 35 | 20 |

In a second embodiment of the invention, the non-alginate polymeric species is one containing $SO_4^{2-}$ groups along the polymer chain. Examples include sulphonated polysaccharides which are naturally occurring elements of tissue (serving to keep water in the tissue). Co-spinning of alginates with sulphated polysaccharides results in materials which may be likened to artificial tissue.

Specific examples of sulphated polysaccharides which may be co-spun with alginate include chondroitin, dermatan, and heparan sulphates as well as heparin. Fibres comprising alginate co-spun with at least one of these polysaccharides provide an ideal matrix for growth of tissue (e.g. skin on a burn).

In a further embodiment of the invention, the non-alginate polymer is uncharged. Examples of such uncharged polymers which may be used include Ace Mannan (e.g. clinical grade material as obtainable from Carrington Laboratories, Dallas, Tex., U.S.A.) or other component of Aloe Vera.

As indicated above, the incorporation of the water soluble non-alginate polymeric species produces fibres having modified properties compared to those containing pure alginate. Whilst we do not wish to be bound by any particular theory, we believe this is because pure alginate fibre has a compact "egg box" structure and the non-alginate polymer can disrupt the regular packing of the alginate materials therefore providing increased swelling and absorbancy capability. In the case of fibres comprising alginate and 15% CMC, we have found that the absorbency of a non-woven dressing produced therefrom was 19 g/g as compared to 17 g/g for a dressing produced from fibres of the alginate which had not been co-spun with the CMC.

Apart from absorbency changes, the non-alginate component may introduce active healing or other medical properties in the dressing. The inclusion of pectin, for example, increases the debridement properties of the dressing.

Fibres in accordance with the invention may be produced by spinning a dope comprising a total dissolved solids content of less than 10% (e.g. about 6%) into an aqueous medium containing cations which will result in the formation of insoluble fibres. The amount of the cation may, for example, be less than 1% by weight.

In the case of non-alginate polymers containing $COO^-$ groups it is preferred that the coagulating cation is calcium. If the non-alginate polymer contains $SO_4^{2-}$ groups, it is preferred that the coagulating cation is zinc because of the greater insolubility of the calcium sulphate bridge which will cause slower ion exchange with ions in wound fluids. However this type of slower ion exchange can effectively be used to 'fine-tune' the exudate handling characteristics. This zinc and calcium for instance behave in opposite ways in sulphated species as compared to carboxylated molecules, i.e. calcium is a more effective cross-link in sulphated molecules whereas zinc is more effective in carboxylated species.

The invention will be illustrated by the following non-limiting Examples.

EXAMPLE 1

This example describes the production of alginate/CMC/pectin fibres.

A spinning dope was prepared by mixing 12 kg of sodium alginate (Protanal LF10/60, (available from Pronova Biopolymers), viscosity in 1% solution between 40 to 60 cps), 1.5 kg of sodium carboxymethyl cellulose and 1.5 kg of high methyloxy pectin in 235 litres of water. After storage at room temperature for two days to remove the bubbles, fibres were produced by extruding the dope through a 40,000 hole spinneret (hole diameter 70 um) at 12 m/min. The as-spun fibres were taken up at 7.2 m/min and then stretched at 80° C. to 9 m/min. The fibres were then washed with water before they were dried by first passing the fibres through an acetone bath and then drying with heated air. Finally, the dry tow was crimped and cut to produce staple fibres. The staple fibres could be carded and needled to form a non-woven felt which could be cut into individual dressings.

EXAMPLE 2

This example describes the production of alginate/CMC fibres.

Example 1 was repeated except that the dope was produced by mixing 13.5 kg of sodium alginate (Protanal LF10/60, viscosity in 1% solution between 40 to 60 cps) and 1.5 kg of sodium carboxymethyl cellulose in 235 litres of water. The fibres could be spun and carded into a non-woven dressing as in Example 1.

The alginate/CMC dressing as produced in this way had an absorbency of 19 g/g as compared to 17 g/g for dressings made from fibres without addition of CMC under exactly the same processing conditions.

EXAMPLE 3

This Example describes the production of alginate/Ace Mannan fibres.

Example 1 was repeated except that the dope was produced by mixing 13.5 kg of sodium alginate (Protanal LF10/60, viscosity in 1% solution between 40 to 60 cps) and 1.5 kg of Ace Mannan (ex-Carrington Laboratories) in 235 litres of water. The fibres could be spun and carded into a non-woven dressing as in Example 1.

What is claimed is:

1. Fibres which have been produced by cospinning of an alginate and at least one water soluble polysaccharide other than an alginate which serves to increase the absorbency of the alginate wherein the fibres include a major proportion of weight of alginate, the alginate is in a cross-linked form and said alginate from which the fibres are cospun has a G-content of 35–70% by weight, an M-content of 65–30% by weight, and a viscosity of 30–100 cP in a 1% water solution.

2. Fibres as claimed in claim 1 comprising 50–95% by weight, based on the weight of the fibres, of alginate.

3. Fibres as claimed in claim 2 comprising 70–95% by weight of alginate and 5–30% by weight of said water soluble polysaccharide, the percentage is being based on the weight of the fibres.

4. Fibres as claimed in claim 1 wherein said water soluble polysaccharide which has been cospun with the alginate has negative charges along a polymer chain.

5. Fibres as claimed in claim 4 wherein the negative charges for the polysaccharide are provided by $COO^-$ groups provided along a polysaccharide chain.

6. Fibres as claimed in claim 5 wherein the polysaccharide is pectin, N—,O-carboxymethyl chitosan, carrageenan, xanthan or gellan.

7. Fibres as claimed in claim 5 wherein the polysaccharide is carboxymethyl cellulose.

8. Fibres as claimed in claim 1 wherein the polysaccharide is a sulphated polysaccharide in which the $SO_4^{2-}$ groups provide negative charges.

9. Fibres as claimed in claim 8 wherein the sulphated polysaccharide is chondroitin sulphate, dermatan sulphate, heparan sulphate or heparin.

10. Fibres as claimed in claim 1 wherein said polysaccharide is uncharged.

11. Fibres as claimed in claim 1 wherein said water-soluble polysaccharide is acemannan.

12. A wound dressing comprising fibres as claimed in claim 1.

13. A method of producing fibres comprising co-spinning an aqueous dope which contains dissolved alginate and at least one dissolved polysaccharide other than an alginate into a coagulation bath which causes cross-linking of the alginate and precipitation of fibres comprised of the alginate and polysaccharide which serves to increase the absorbency of the alginate, wherein the alginate is one having a G-content of 35–70% by weight, an M-content of 65–30% by weight, and a viscosity 30 to 100 cP in a 1% water solution and the fibres include a major proportion by weight of alginate.

14. A method as claimed in claim 13 wherein the alginate has a G-content of 35–70% and correspondingly an M-content of 65–30% by weight.

15. A method as claimed in claim 13 wherein the fibres comprise 50–95% by weight, based on the weight of the fibres, of alginate.

16. A method as claimed in claim 15 wherein the fibres comprise 70–95% by weight of alginate and 5–30% by weight of said water soluble polysaccharide, the percentage is being based on the weight of the fibres.

17. A method as claimed in claim 13 wherein said water soluble polysaccharide has negative charges along a polymer chain.

18. A method as claimed in claim 17 wherein the negative charges for the polysaccharide are provided by $COO^-$ groups provided along a polysaccharide chain.

19. A method as claimed in claim 18 wherein the polysaccharide is pectin, carboxymethyl cellulose, N—,O-carboxymethyl chitosan, carrageenan, xanthan or gellan.

20. A method as claimed in claim 18 wherein the polysaccharide is carboxymethyl cellulose.

21. A method as claimed in claim 19 wherein the polysaccharide is a sulphated polysaccharide in which the $SO_4^{2-}$ groups provide negative charges.

22. A method as claimed in claim 21 wherein the sulphated polysaccharide is chondroitin sulphate, dermatan sulphate, heparan sulphate or heparin.

23. A method as claimed in claim 13 wherein said polysaccharide is uncharged.

24. A method as claimed in claim 23 wherein said water-soluble polysaccharide is acemannan.

25. A method as claimed in claim 13 wherein the dope has a total dissolved solids content of less than 10% by weight.

26. A method as claimed in claim 25 wherein the dope has a total dissolved solids content of about 6% by weight.

27. A method as claimed in claim 13 wherein the coagulation bath contains calcium ions to precipitate the fibres.

28. A method as claimed in claim 13 wherein the alginate has been precipitated with calcium ions.

* * * * *

UNITED STATES PATENT AND TRADEMARK OFFICE
CERTIFICATE OF CORRECTION

PATENT NO. : 6,080,420
DATED : June 27, 2000
INVENTOR(S) : Yimin Qin; Denis Keith Gilding It is certified that error appears in the above-identified patent and that said Letters Patent is hereby corrected as shown below:

In column 4, line 14, please change "of" to --by--.

In column 4, line 45, please change "1" to --10--.

In column 4, line 62, please insert a space after "of".

In column 5, line 14, please change "19" to --17--.

Signed and Sealed this

Fifteenth Day of May, 2001

Attest:

NICHOLAS P. GODICI

Attesting Officer     *Acting Director of the United States Patent and Trademark Office*